United States Patent
Kirsch et al.

(10) Patent No.: US 11,812,948 B2
(45) Date of Patent: Nov. 14, 2023

(54) SUTURE PACKAGING

(71) Applicant: Covidien LP, Mansfield, MA (US)

(72) Inventors: David Kirsch, Madison, CT (US); Guido Pedros, Shelton, CT (US)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 17/884,376

(22) Filed: Aug. 9, 2022

(65) Prior Publication Data
US 2022/0378419 A1 Dec. 1, 2022

Related U.S. Application Data

(63) Continuation of application No. 16/693,815, filed on Nov. 25, 2019, now Pat. No. 11,406,376, which is a
(Continued)

(51) Int. Cl.
*A61B 17/06* (2006.01)
*B65D 25/10* (2006.01)
(Continued)

(52) U.S. Cl.
CPC .. *A61B 17/06123* (2013.01); *A61B 17/06114* (2013.01); *A61B 17/06133* (2013.01);
(Continued)

(58) Field of Classification Search
CPC ........ A61B 17/06123; A61B 17/06114; A61B 17/06133; A61B 2017/06142;
(Continued)

(56) References Cited

U.S. PATENT DOCUMENTS 1,627,757 A 5/1927 Elm
2,615,565 A 10/1952 Bower et al.
(Continued)

FOREIGN PATENT DOCUMENTS

DE 4220407 C1 11/1993
DE 19744543 A1 4/1999
(Continued)

OTHER PUBLICATIONS

European Search Report for EP 09252350.5-1269 dated Dec. 1, 2009 (3 pages).

*Primary Examiner* — Robert Poon
(74) *Attorney, Agent, or Firm* — WEBER ROSSELLI & CANNON LLP

(57) ABSTRACT

A suture package for retaining a barbed suture is provided. The suture package includes a suture retaining member including an outer wall and an inner wall. The inner wall is radially spaced from the outer wall and defines a suture retaining area therebetween. The inner wall defines a needle retaining area and includes at least one opening therein to permit reception of at least one suture therethrough. The outer wall includes a plurality of inwardly extending tabs configured to engage a cover. The suture package further includes a cover configured to be received within the outer wall of the suture retaining member and to selectively engage the inwardly extending tabs formed thereon.

13 Claims, 4 Drawing Sheets

Related U.S. Application Data continuation of application No. 15/470,973, filed on Mar. 28, 2017, now Pat. No. 10,517,586, which is a continuation of application No. 12/567,884, filed on Sep. 28, 2009, now Pat. No. 9,622,743.

(60) Provisional application No. 61/102,066, filed on Oct. 2, 2008.

(51) Int. Cl.
 *B65D 25/54* (2006.01)
 *B65D 43/02* (2006.01)

(52) U.S. Cl.
 CPC ...... *A61B 17/06166* (2013.01); *B65D 25/108* (2013.01); *B65D 25/54* (2013.01); *B65D 43/02* (2013.01); *A61B 2017/06142* (2013.01); *A61B 2017/06147* (2013.01); *B65D 2543/00268* (2013.01); *B65D 2543/00833* (2013.01)

(58) Field of Classification Search
 CPC ........... A61B 2017/06057; A61B 2017/06147; B65D 77/2016
 See application file for complete search history.

(56) References Cited

U.S. PATENT DOCUMENTS

| | | | |
|---|---|---|---|
| 3,233,819 A | 2/1966 | Flaherty | |
| 3,298,505 A | 1/1967 | Stephenson | |
| 3,464,832 A * | 9/1969 | Mullinix | B65D 77/2032 229/125.05 |
| 3,495,703 A | 2/1970 | Calabrese | |
| 3,749,238 A * | 7/1973 | Taylor | A61B 17/06123 206/484 |
| 3,885,731 A | 5/1975 | Mullinix | |
| 3,972,418 A | 8/1976 | Schuler et al. | |
| 4,424,898 A * | 1/1984 | Thyen | A61B 17/06133 206/380 |
| 4,433,808 A | 2/1984 | Gordon et al. | |
| 4,453,666 A * | 6/1984 | Gordon | B65D 47/0833 229/125.17 |
| 4,699,271 A | 10/1987 | Lincoln et al. | |
| 4,819,794 A | 4/1989 | Silverstein et al. | |
| 4,961,498 A | 10/1990 | Kalinski et al. | |
| 4,967,902 A | 11/1990 | Sobel et al. | |
| 5,052,551 A | 10/1991 | Cerwin et al. | |
| 5,056,658 A | 10/1991 | Sobel et al. | |
| 5,099,994 A | 3/1992 | Kalinski et al. | |
| 5,154,283 A | 10/1992 | Brown | |
| 5,165,217 A | 11/1992 | Sobel et al. | |
| 5,213,210 A | 5/1993 | Cascio et al. | |
| 5,228,565 A | 7/1993 | Sinn | |
| 5,230,424 A * | 7/1993 | Alpern | A61B 17/06133 206/227 |
| 5,236,083 A | 8/1993 | Sobel et al. | |
| 5,249,673 A | 10/1993 | Sinn | |
| 5,271,495 A * | 12/1993 | Alpern | A61B 17/06133 206/380 |
| 5,284,240 A | 2/1994 | Alpern et al. | |
| 5,350,060 A | 9/1994 | Alpern et al. | |
| 5,392,903 A | 2/1995 | Sinn | |
| 5,462,162 A | 10/1995 | Kaplan et al. | |
| 5,472,081 A | 12/1995 | Kilgrow et al. | |
| 5,575,382 A | 11/1996 | Sobel et al. | |
| 5,628,395 A | 5/1997 | Daniele et al. | |
| 5,655,652 A | 8/1997 | Sobel et al. | |
| 5,657,894 A | 8/1997 | Bowen | |
| 5,833,055 A * | 11/1998 | Cerwin | A61B 17/06133 383/211 |
| 5,887,706 A | 3/1999 | Pohle et al. | |
| 5,906,273 A | 5/1999 | Pohle et al. | |
| 6,047,815 A | 4/2000 | Cerwin et al. | |
| 6,076,659 A | 6/2000 | Baumgartner et al. | |
| 6,135,272 A | 10/2000 | Sobel et al. | |
| 6,260,699 B1 | 7/2001 | Kaplan et al. | |
| 6,463,719 B2 | 10/2002 | Dey et al. | |
| 6,464,071 B2 | 10/2002 | Baumgartner | |
| 6,481,568 B1 | 11/2002 | Cerwin et al. | |
| 6,533,112 B2 | 3/2003 | Warnecke | |
| 6,644,469 B2 | 11/2003 | Alpern | |
| 6,804,937 B2 | 10/2004 | Dey et al. | |
| 8,459,446 B2 | 6/2013 | Kozlowski | |
| 9,622,743 B2 | 4/2017 | Kirsch et al. | |
| 10,517,586 B2 * | 12/2019 | Kirsch | B65D 43/02 |
| 2002/0139804 A1 | 10/2002 | Greiner | |
| 2003/0111471 A1 | 6/2003 | Gritner | |
| 2004/0050721 A1 * | 3/2004 | Roby | A61B 17/06133 206/63.3 |
| 2005/0035007 A1 | 2/2005 | Kennedy et al. | |
| 2006/0226031 A1 | 10/2006 | Kennedy et al. | |
| 2007/0227914 A1 * | 10/2007 | Cerwin | A61B 17/06133 206/63.3 |
| 2007/0256945 A1 | 11/2007 | Kennedy et al. | |
| 2008/0185752 A1 | 8/2008 | Cerwin et al. | |
| 2009/0205987 A1 | 8/2009 | Kennedy et al. | |
| 2009/0250356 A1 | 10/2009 | Kirsch et al. | |
| 2010/0140115 A1 | 6/2010 | Kirsch | |
| 2010/0170812 A1 | 7/2010 | Odierno | |

FOREIGN PATENT DOCUMENTS

| | | |
|---|---|---|
| EP | 0726062 A2 | 8/1996 |
| EP | 0760228 A1 | 3/1997 |

* cited by examiner

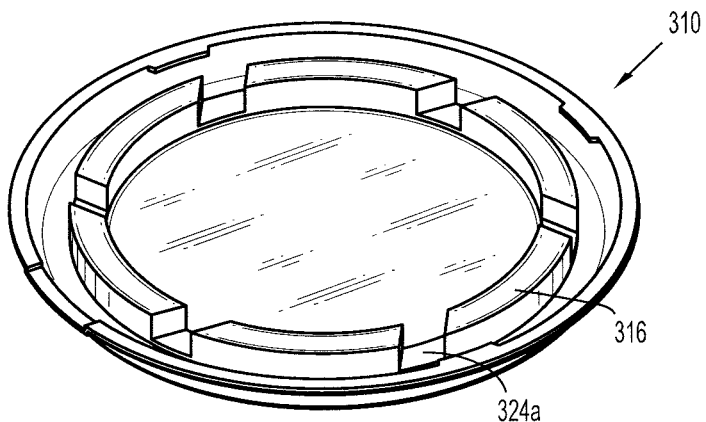
FIG. 5a
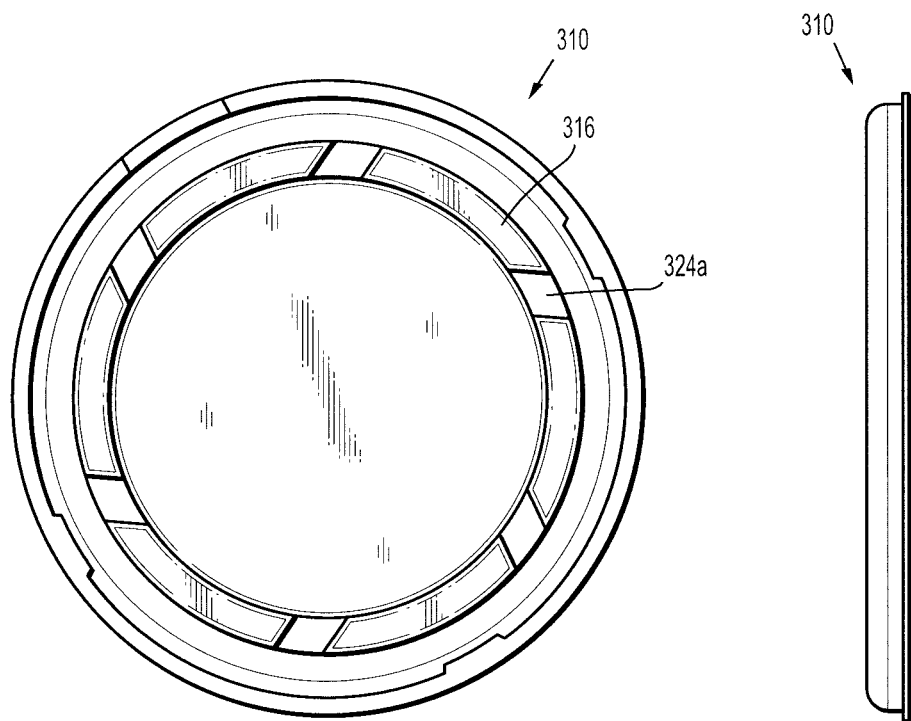
FIG. 5b   FIG. 5c

SUTURE PACKAGING

CROSS-REFERENCE TO RELATED APPLICATION

This application is a continuation of U.S. patent application Ser. No. 16/693,815 filed Nov. 25, 2019, now U.S. Pat. No. 11,406,376, which is a continuation of U.S. patent application Ser. No. 15/470,973 filed Mar. 28, 2017, now U.S. Pat. No. 10,517,586, which is a continuation of U.S. patent application Ser. No. 12/567,884 filed Sep. 28, 2009, now U.S. Pat. No. 9,622,743, which claims benefit of and priority to U.S. Provisional Application Ser. No. 61/102,066 filed Oct. 2, 2008, the entire content of which is incorporated herein by reference.

BACKGROUND

Technical Field

The present disclosure relates to packaging for sutures. More particularly, the present disclosure relates to suture packages for receiving barbed sutures.

Background of Related Art

Sutures and packages for retaining sutures are known in the art. Suture packages may be of the foldable type, constructed from paper and configured to form a pocket for receiving one or more sutures therein. Alternatively, suture packages may be of the molded variety. Such packages typically define a channel for the receipt of one or more sutures therein.

Packaging barbed sutures is complicated due to the configuration of the sutures. The barbs formed along the length of a barbed suture may increase the likelihood that the suture will become entangled with itself or other barbed sutures. When excessive force is applied to the barbs while untangling the suture, damage may result to the suture barbs, thereby diminishing the effectiveness of the suture.

Therefore, it would be beneficial to have a suture package configured to retain one or more barbed sutures such that the suture does not become entangled. It would be further beneficial if the suture package is configured to prevent the barbs from being flatten or otherwise damaged.

SUMMARY

Accordingly, a suture package for retaining a barbed suture is provided. The suture package includes a suture retaining member including an outer wall and an inner wall. The inner wall is radially spaced from the outer wall and defines a suture retaining area therebetween. The inner wall defines a needle retaining area and includes at least one opening therein to permit reception of at least one suture therethrough. The outer wall includes a plurality of inwardly extending tabs configured to engage a cover. The suture package further includes a cover configured to be received within the outer wall of the suture retaining member and to selectively engage the inwardly extending tabs formed thereon.

In one embodiment, the suture retaining member may be rigid. The suture retaining member may comprise a polymer. The cover may comprise paper. The needle retaining area may include at least one needle park. The needle retaining area may include three needle parks. The needle retaining area may include a foam member configured to receive a needle.

In another embodiment, the cover may further include a tab configured for operable engagement by a clinician. The outer wall of the suture retaining member may include a recessed portion configured to receive the tab formed in the cover. The cover may include a cut-out configured for operable engagement by a clinician. The cut-out may also be configured for viewing at least a portion of the suture retaining area. The inner wall may be formed from a plurality of protrusions. At least one of the protrusions may be curved inward to receive an end of a suture thereabout. At least one of the protrusions may include a slot configured to securely receive an end of a suture therethrough. The slot may be configure to securely receive an end effector formed on an end of a suture. The suture retaining member may be configured to engage a suture loading apparatus. The suture retaining member may include openings configured to receive mounting pins of a suture loading apparatus. The cover may include openings to engage mounting pins of a suture loading apparatus.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIGS. 5A-5C are perspective (FIG. 5A), top (FIG. 5B) and side (FIG. 5C) views of a suture retaining member according to another embodiment of a suture package of the present disclosure.

DETAILED DESCRIPTION

The following description will describe various embodiments of a suture package. Although continued reference will be made to a barbed suture 5 (FIG. 2), having an end effector 6 on a first end, a needle 7 on an opposite end, and barbs 8 formed along the length thereof, it is envisioned that the aspects of the present disclosure may be modified for use with sutures of all configurations and should not be limited to the embodiments herein described.

Figure 1A:
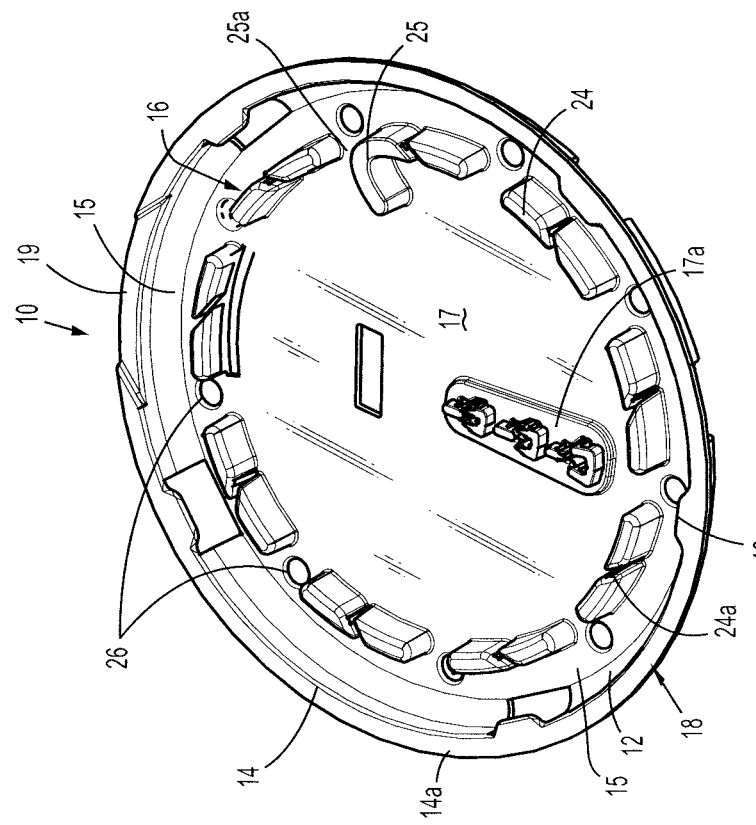
FIG. 1A is a perspective view of a suture retaining member according to an embodiment of a suture package of the present disclosure.
Figure 1B:
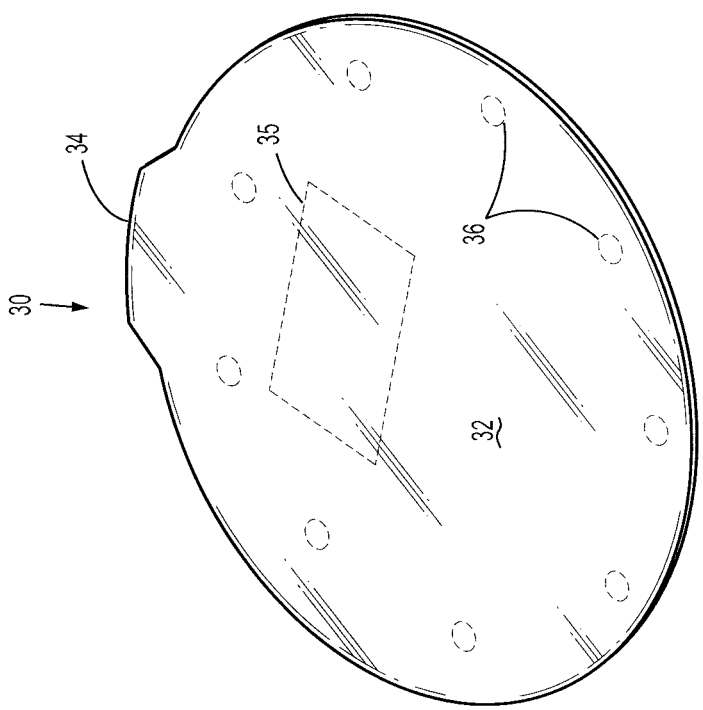
FIG. 1B is a perspective view of a cover for the a suture retaining member of FIG. 1.
Figure 2:
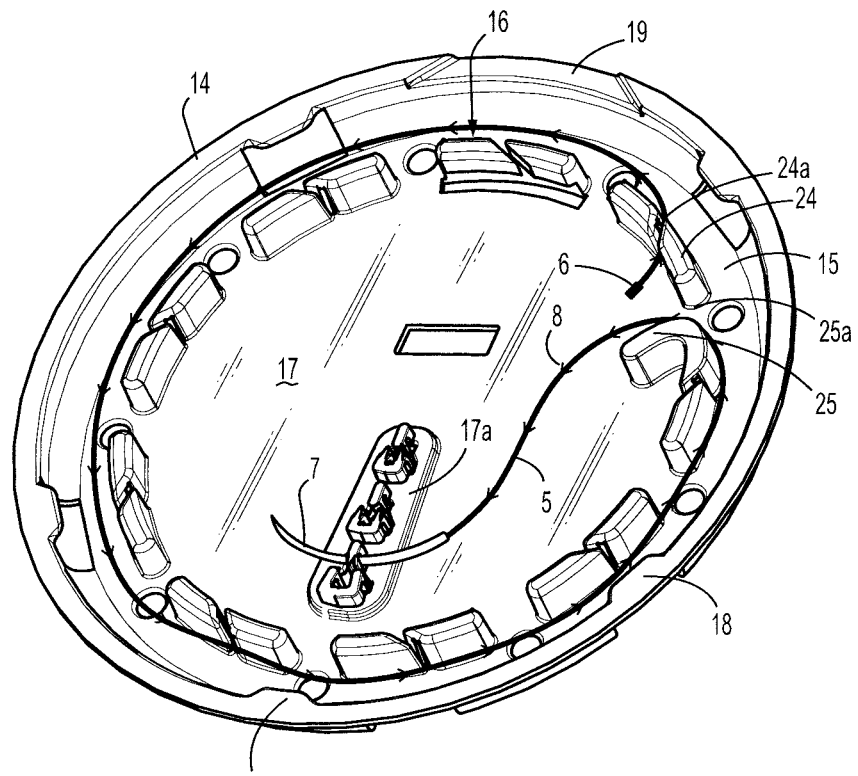
FIG. 2 is a perspective view of the suture retaining member of FIG. 1A, including a barbed suture.

With reference to FIGS. 1A and 1B, suture package 100 (FIG. 3) includes a substantially rigid suture retaining member 10 (FIG. 1A) and a cover 30 (FIG. 1B). Suture retaining member 10 may be composed of polymers or other suitable material. Suture retaining member 10 is configured to retain one or more barbed sutures 5 (FIG. 2). Cover 30 is configured to selectively engage suture retaining member 10, thereby creating a closed suture retaining area 15 for maintaining suture 5 with suture retaining member 10.

With reference to FIG. 1B, cover 30 defines a substantially planar member 32 configured to selectively engage suture retaining member 10. As shown, cover 30 defines a substantially circular configuration, however, cover 30 may be formed to fit a suture retaining member of any configuration, including oval, octagonal and rectangular configurations. Cover 30 may be formed of cardboard, heavy paper, semi-flexible plastic or any other suitable material. Cover 30 includes one or more tabs 34. As will be discussed in further detail below, tab 34 is configured for engagement by a user to facilitate separation of cover 30 from suture retaining member 10.

With reference still to FIG. 1B, cover 30 may also include a cut-out or window 35 (shown in phantom). Cut-out 35 is configured for viewing of indicia located on suture retaining member 10 and/or viewing the contents of suture retaining member 10. Alternatively, or in addition, cut-out 35 may be configured for engagement by a user to facilitate removal of cover 30 from suture retaining member 10. Cover 30 may further include a plurality of openings 36 (shown in phantom) radially spaced about a perimeter of cover 30. As will be discussed in further detail below, openings 36 are aligned with openings 26 formed in suture retaining member 10 and are sized to engage mounting pins (not shown) of a suture loading apparatus (also not shown).

Turning to FIG. 1A, suture retaining member 10 includes a substantially planar base 12, an outer wall 14, and an inner wall 16. Outer wall 14 extends about a perimeter of base 12 to define a first wall of a suture retaining portion 15. Inner wall 16 is spaced radially inward of outer wall 14. Inner wall 16 forms a second wall defining suture retaining portion 15. A needle retaining area 17 is formed interior to inner wall 16. In one embodiment, a needle park 17a is integrally formed with planar base 12. Needle park 17a may be configured to receive one or more suture needles of various sizes and configurations. In an alternative embodiment, needle park 17a may be secured to planar base 12 using adhesive, glue, ultrasonic welding or the like. In another embodiment, suture needle 7 (FIG. 2) may be loosely received within needle retaining area 17.

With reference still to FIG. 1A, outer wall 14 includes a plurality of inwardly extending tabs 18 formed on a top surface 14a thereof. Tabs 18 are configured to engage cover 30 when cover 30 is received within outer wall 14. A notched or recessed portion 19 is formed on top surface 14a of outer wall 14. As will be discussed in further detail below, recessed portion 19 is configured to receive tab 34 of cover 30 when cover 30 is engaged with tabs 18 of outer wall 14.

Figure 3:
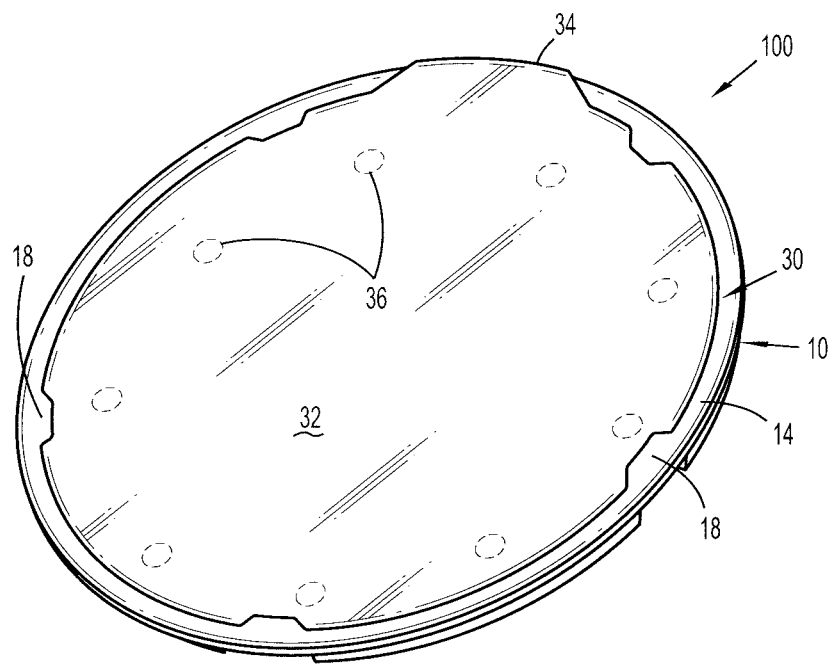
FIG. 3 is a perspective view of a suture package according to an embodiment of the present disclosure, including the suture retaining member of FIG. 1A and the cover of FIG. 1B.

Still referring to FIG. 1A, as discussed above, inner wall 16 is radially spaced from outer wall 14 to form suture retaining area 15. The greater the distance of inner wall 16 from outer wall 14, the larger suture retaining area 15. Suture retaining area 15 may be configured to receive one or more sutures 5 (FIG. 2). Inner wall 16 is formed by a series of spaced protrusions 24. At least one of protrusions 24 includes a slot 24a which, in some embodiments, may be configured to receive distal end 6 of suture 5. At least one of protrusions 24 includes an inwardly curved protrusion 25 configured to form an opening 25a into needle retaining area 17. In this manner, when the body portion of suture 5 is retained within suture retaining area 15, the end of suture 5 including needle 7 may be received through opening 25a such that needle 7 may be received within needle retaining area 17. Protrusions 24 are of sufficient height to support cover 30 when cover 30 is selectively engaged with tabs 18 of outer wall 14 (FIG. 3). In this manner, when suture 5 is retained within suture retaining area 15, barbs 8 are not flattened by cover 30 when cover 30 is selective engaged with suture retaining member 10.

With reference still to FIG. 1A, suture retaining member 10 further includes a plurality of openings 26 radially spaced about planar base 12. Openings 26 are configured to engage mounting pins (not shown) of a suture loading apparatus (also not shown). Openings 26 may be, as shown, located within the spaces between protrusions 24, or alternatively, openings 26 may be formed in suture retaining area 15 and/or needle retaining area 17.

The loading of a suture 5 within suture package 100 will now be described in detail with reference to FIG. 2. To facilitate loading of suture 5 within suture retaining member 10, suture retaining member 10 may be received on a suture loading apparatus (not shown). In this manner, suture retaining member 10 is placed on the suture loading apparatus such that mounting pins (not shown) engage openings 26 formed in suture retaining member 10. Initially, the end of suture 5 including end effector 6 is received within slot 24a formed within one of protrusions 24 extending from planar base 12. Alternatively, the end of suture 5 including end effector 6 may be loosely received within suture retaining area 15.

With reference still to FIG. 2, the body portion of suture 5 is next received within suture retaining area 15. Suture 5 is then wound in around inner wall 16 of suture retaining member 10 to receive suture 5 within suture retaining area 15. Suture 5 may be rotated about inner wall 16 in a clockwise direction, or instead, as shown, in a counterclockwise direction. Alternatively, suture retaining member 10 may be rotated in a clockwise direction, either manually or through the operation of the suture loading apparatus to wind suture 5 about inner wall 16. The direction suture 5 is wound about inner wall 16 is generally determined by the configuration of curved protrusion 25. Suture 5 is wound in a direction that enables suture 5 to be inserted through opening 25a and wrapped about curved protrusion 25. In this manner, suture 5 is prevented from creasing or folding at needle 7 is received within needle retaining area 17. Suture 5 may be wound about inner wall 16 of suture retaining member 10 one or more times, depending on the length of suture 5.

Still referring to FIG. 2, the body portion of suture 5 is received within suture retaining area 15, the end portion of suture 5 containing needle 7 is then received through opening 25a formed by curved protrusion 25 such that needle 7 is received within needle retaining area 17. Needle 7 then is then selectively engaged with needle park 17a.

Turning now to FIG. 3, once suture 5 is received within suture retaining area 15 of suture retaining member 10, cover 30 is placed onto suture retaining member 10. When a suture loading apparatus (not shown) is used, the alignment pins (not shown) extending through openings 26 formed in suture retaining member 10 align tab 34 of cover 30 with recessed portion 19 of suture retaining member 10. Absent the suture loading apparatus, tab 34 of cover 30 must be manually aligned with recessed portion 19 of suture retaining member 10. To secure cover 30 within suture retaining member 10 an outer rim of cover 30 is received under inwardly extending tabs 18 formed on outer wall 14 of suture retaining member 10. In this manner, cover 30 engages a top surface of inner wall 16 to secure suture 5 within suture retaining area 15 and needle 7 within needle retaining area 17. Suture package 100 may then be removed from the suture loading apparatus and hermetically sealed in sterile packaging (not shown).

To remove suture 5 from suture packaging 100, suture packaging 100 is first removed from any packaging in which it might be encased. A clinician next holds suture retaining member 10 in a first hand about outer wall 14 while gripping tab 34 formed on cover 30. The engagement of tab 34 by the clinician is facilitated through the overlap of tab 34 with outer wall 14. Tab 34 of cover 30 is then pulled away from suture retaining member 10 to disengage cover 30 from inwardly extending tabs 18 formed on outer wall 14, thereby separating cover 30 from suture retaining member 10 and exposing suture 5. In an alternate embodiment, the clinician inserts one or more fingers through cut-out 35 in cover 30 to separate cover 30 from suture retaining member 10.

A clinician may then manually grasp needle 7 by hand or with forceps or other grasping instrument, to remove needle 7 from needle park 17a. Continued pulling on needle 7 causes suture 5 to be withdrawn from opening 25a and released from suture retaining portion 15. If the end of suture 5 including end effector 6 is secured within slot 24a of protrusion 24, then the clinician may have to separate suture 5 from suture retaining member 10 manually, otherwise, suture 5 should easily withdraw from suture retaining area 15 without becoming entangled.

Figure 4:
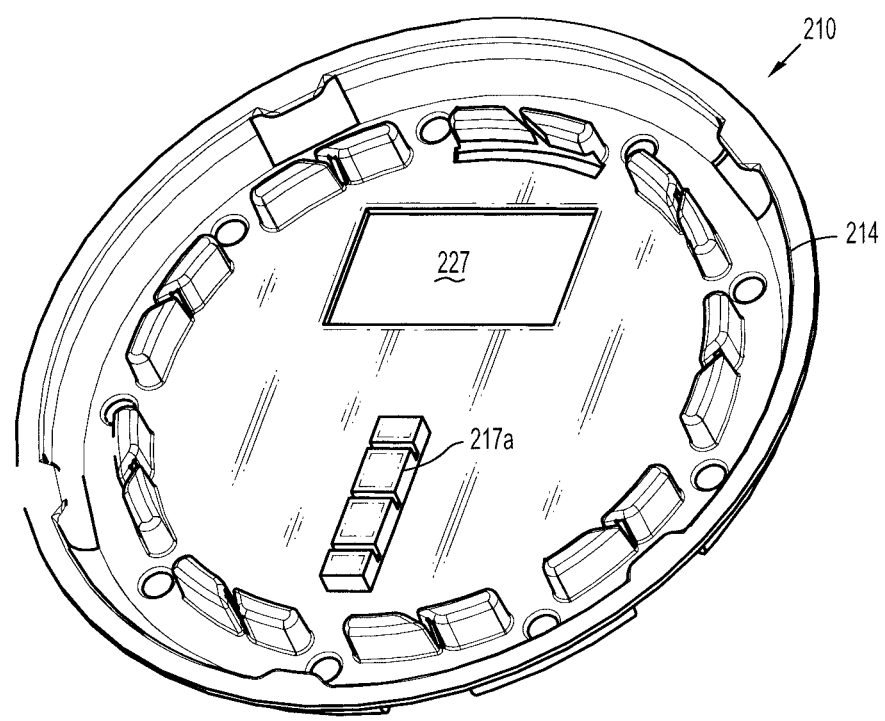
FIG. 4 is a perspective view of a suture retaining member of a suture package according to another embodiment of the present disclosure.

With reference now to FIG. 4, an alternate embodiment of a suture retaining member is shown generally as suture retaining member 210. Suture retaining member 210 is substantially similar to suture retaining member 10. Therefore, the following discussion will relate only to the differences therebetween. Similar reference numerals refer to similar structure throughout the embodiments. Suture retaining member 210 includes an opening 227 of sufficient size to permit viewing of indicia printed on an inward facing surface (not shown) of cover 30. Suture retaining member 210 further includes a foam member 217a configured to receive one or more suture needles 7.

Turning to FIGS. 5A-5C, a suture retaining member according to another embodiment of the present disclosure is shown generally as suture retaining member 310. Suture retaining member 310 is substantially similar to suture retaining member 10 and 210 described herein above. Suture retaining member 310 includes an annular inner wall 316 defining a series of slots or openings 324a. Slots 324a are configured to receive a first and/or second end of a suture that has been wrapped around inner wall 316. Placement of the first and/or second end of a suture through slots 324a facilitate removal of the suture from suture retaining member 310. Suture retaining member 310 is configured to selectively engage a paper or cardboard cover (not shown) to retain a suture about inner wall 316.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. A method of unloading a suture from a suture package, the suture including a first end portion and a second end portion opposite the first end portion, and the suture package including a suture retaining member and a cover, the suture retaining member having a base, an outer wall, and an inner wall, the outer wall extending about a perimeter of the base defining a first wall of a suture retaining area, the inner wall being formed from a plurality of protrusions extending from the base and radially spaced inwardly from the outer wall and defining the suture retaining area therebetween, the inner wall defining a needle retaining area and including at least one opening to permit passage of the first end portion of the suture therethrough, wherein the second end portion of the suture is secured in a slot defined in at least one of the protrusions, the method comprising the steps of:

separating the cover from the suture retaining member; and removing the second end portion of the suture from the slot defined in at least one of the protrusions and the first end portion of the suture from the needle retaining area and the opening.

2. The method of claim 1, wherein the cover further comprises a cut-out configured for operable engagement by a user.

3. The method of claim 2, further comprising engaging the cut-out of the cover prior to separating the cover from the suture retaining member.

4. The method of claim 3, wherein engaging the cut-out includes inserting one or more fingers of the user through the cut-out in the cover.

5. The method of claim 2, wherein the cut-out is configured for viewing indicia located on the suture retaining member or viewing contents within the suture retaining member.

6. The method of claim 5, wherein the suture retaining member further comprises a plurality of aligned needle parks secured directly to or integrally formed with the base within the needle retaining area.

7. The method of claim 6, wherein the first end portion of the suture includes a needle and removing the suture further comprises grasping, by hand or with an instrument, the needle to free the needle of the needle park and withdraw the needle and suture from the retaining member.

8. The method of claim 1, wherein the suture retaining member and the cover are substantially circular and the base and the cover are generally planar.

9. The method of claim 1, further comprising the step of holding the suture retaining member prior to separating the cover.

10. The method of claim 1, wherein the suture further comprises an end effector on the second end portion of the suture.

11. The method of claim 10, further comprising removing the end effector on the second end portion of the suture, from the needle retaining area.

12. The method of claim 1, wherein the suture further comprises a body portion between the first and second end portions of the suture.

13. The method of claim 12, further comprising removing the body portion of the suture from the suture retaining area.

* * * * *